(12) United States Patent
Carrez et al.

(10) Patent No.: US 8,783,262 B2
(45) Date of Patent: *Jul. 22, 2014

(54) IMPROVEMENTS TO OPERATING DRAPES WITH WINDOW

(75) Inventors: Jean-Luc Carrez, Ecouen (FR); Xavier Hocq, Coye la Foret (FR); Patrick Lestoquoy, Attiches (FR)

(73) Assignee: Vygon, Ecouen (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/668,738

(22) PCT Filed: Jul. 15, 2008

(86) PCT No.: PCT/EP2008/059238
§ 371 (c)(1),
(2), (4) Date: Jan. 12, 2010

(87) PCT Pub. No.: WO2009/010509
PCT Pub. Date: Jan. 22, 2009

(65) Prior Publication Data
US 2010/0186754 A1 Jul. 29, 2010

(30) Foreign Application Priority Data
Jul. 16, 2007 (FR) ...................................... 07 56518

(51) Int. Cl.
*A61B 19/08* (2006.01)
(52) U.S. Cl.
USPC .......................................... 128/853; 128/849
(58) Field of Classification Search
CPC .... A61B 19/08; A61B 19/081; A61B 19/087; A61B 19/088; A61B 19/10; A61B 2019/08; A61B 2019/081; A61B 2019/10; A61B 2019/103

USPC .................. 128/849–857; 600/119, 124–125; 604/171, 160–163

See application file for complete search history.

(56) References Cited

U.S. PATENT DOCUMENTS

| | | | | | |
|---|---|---|---|---|---|
| 3,565,067 | A | * | 2/1971 | Bayer et al. | 128/853 |
| 4,600,001 | A | * | 7/1986 | Gilman | 602/52 |
| 4,915,102 | A | * | 4/1990 | Kwiatek et al. | 604/307 |
| 5,109,873 | A | | 5/1992 | Marshall | |
| 5,127,423 | A | * | 7/1992 | Draeger | 128/849 |
| 5,494,050 | A | * | 2/1996 | Reyes | 128/849 |
| 5,515,868 | A | * | 5/1996 | Mills | 128/854 |
| 6,105,579 | A | * | 8/2000 | Levitt et al. | 128/849 |
| 6,966,320 | B1 | * | 11/2005 | Baynes | 128/853 |
| 7,086,404 | B2 | * | 8/2006 | Dusenbery et al. | 128/853 |
| 7,588,034 | B2 | * | 9/2009 | Mathis et al. | 128/849 |
| 2004/0166262 | A1 | * | 8/2004 | Busche et al. | 428/34.9 |
| 2009/0277460 | A1 | * | 11/2009 | Carrez et al. | 128/853 |

FOREIGN PATENT DOCUMENTS

| | | |
|---|---|---|
| DE | 8904426 U1 | 5/1989 |
| WO | 9904721 A1 | 2/1999 |
| WO | 9916377 A1 | 4/1999 |

* cited by examiner

*Primary Examiner* — Patricia Bianco
*Assistant Examiner* — Kari Petrik
(74) *Attorney, Agent, or Firm* — Levine Mandelbaum PLLC

(57) ABSTRACT

A surgical drape has an impermeable cloth with a window providing access to the surgical site. The cloth has two peelable impermeable films which are a continuation of one another and are sealed together by a heat weld making it possible to separate the films by peeling. The window is shared between the two sheets. The invention has application in surgical drapes used in operations.

9 Claims, 4 Drawing Sheets

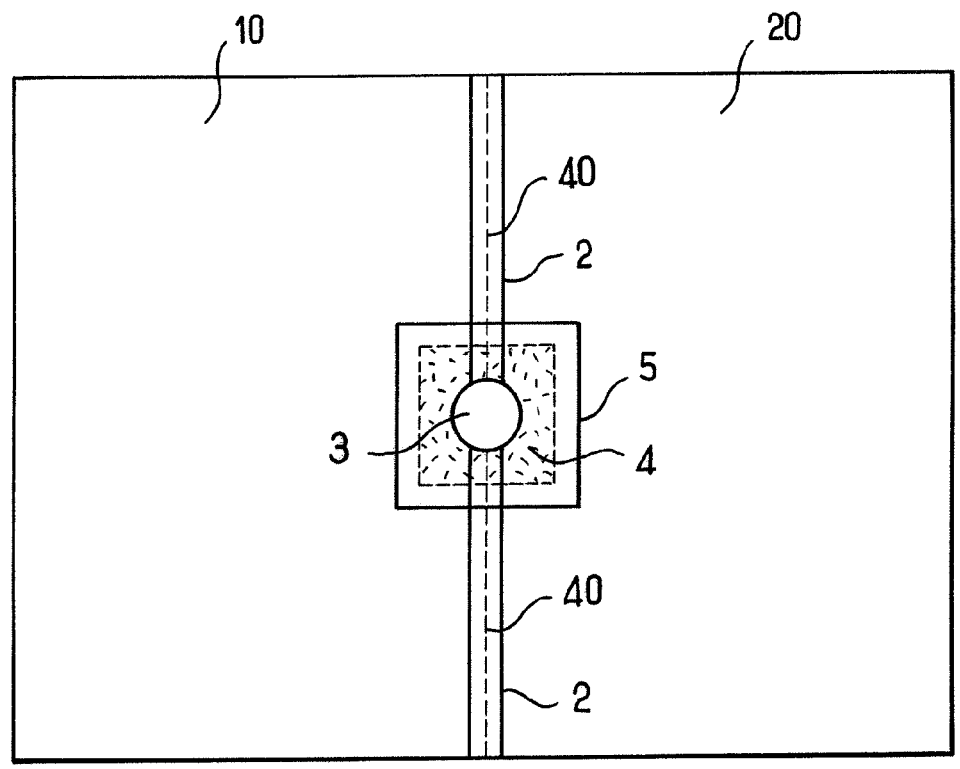
FIG_3
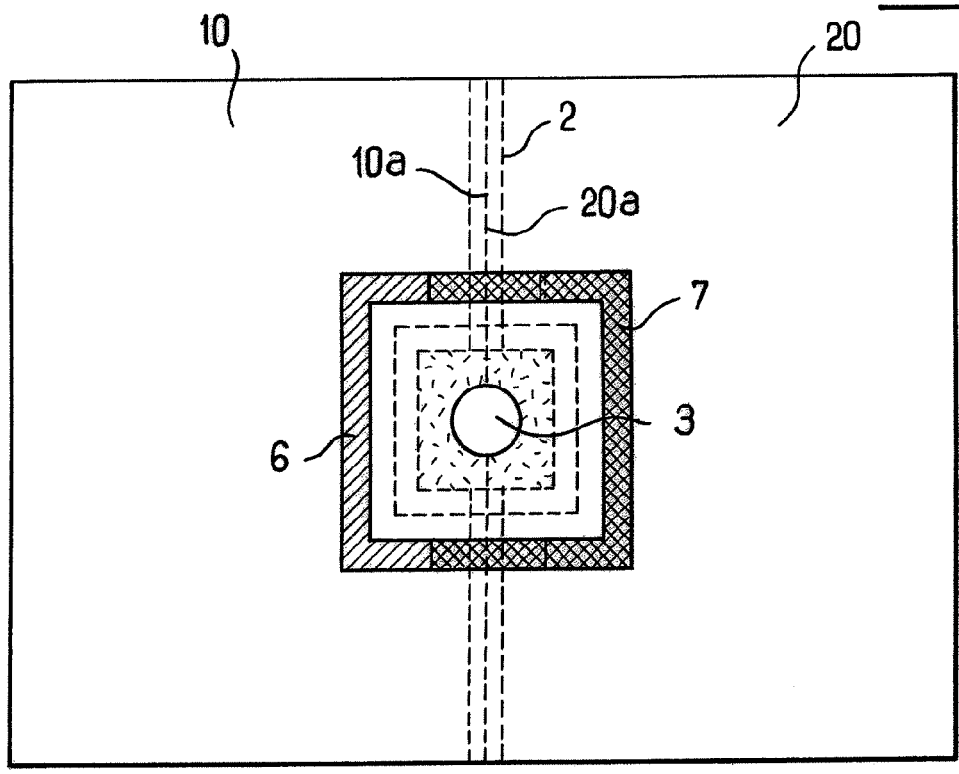
FIG_4

IMPROVEMENTS TO OPERATING DRAPES WITH WINDOW

BACKGROUND OF THE INVENTION

The invention relates to an impermeable operating drape which includes a window through which an operator may access a surgical site and introduce into the body of a patient a tube or wire optionally extended with a perfusion line or another line which should remain in place when the drape has to be removed.

In order to remove the drape in spite of the presence of the tube, of the wire or of the line which passes through the window, it is known from the prior art how to cut the drape by means of an instrument or how to tear it at the moment intended for removing it, until the window is opened laterally. These operations complicate the work of the operator and constitute a risk for the tube, the wire or the line.

In order to facilitate these operations, it was proposed to provide the drape with cutting or tearing slits or lines, as described for example in documents EP 1 009 318 and WO 99/16377.

Document WO 99/16377 describes drapes with windows used in ophthalmology in which lines are formed which join on the window and which allow the drape to be subsequently torn in order to adapt it more easily to the shape of the face, and notably of the eyebrows and eyelids of the patient. These lines are formed with perforations or indentations or weakening lines of the film. In fact, the only method actually described is the cutting of perforations with a rotary knife.

On the other hand, if a drape with a line of pre-cut dots may allow separation, it is not impermeable around the surgical site. Now, it should be impermeable for reasons of asepsis and of possible infections. The indentations or thermal weakening embrittle the drape and promote accidental formation of perforations.

SUMMARY OF THE INVENTION

An object of the invention is to provide an operating drape with a window for the operation, a drape which may then separated into two portions in order to remove it in spite of the presence of tubing coming out of the surgical site through the window and connected to apparatuses, while ensuring impermeability without embrittling the drape, and to separate the drape into two without the assistance of a cutting tool.

For this purpose, a an operating drape is provided according to the invention, comprising an impermeable cloth having a window for accessing the surgical site, the cloth including two peelable impermeable films maintained in the extension of each other in a sealed manner by means of a heat weld making it possible to separate the film by peeling, the window being shared between both films.

Thus, the use of peelable impermeable films maintained in the extension of each other in a sealed manner by a heat weld enables films to be separated from each other in a simple way, with least effort, without the use of cutting tools and on the other hand, the seal may be ensured and therefore the impermeability of the drape in particular around the surgical site.

Advantageously, but optionally, the operating drape has at least one of the following features:
- both films have two joining edges maintained by a pealable impermeable strip placed under the edges and to which the edges are attached by the heat weld;
- both films have two superposed edges and the heat weld is achieved between the edges;
- the edges are rectilinear;
- said window is substantially half-shared between both films;
- the films are rectangular;
- the drape comprises absorbent means around the window, slit for lateral peeling;
- the absorbing means comprise two mating absorbent strips for forming a frame around the window and overlapping, both strips being adhesively bonded to the drape except in locations where both strips overlap so that they remain free in these locations;
- the absorbent strips are U-shaped;
- the drape includes several superposed windows with decreasing sizes made in successive peelable masks which are slit for lateral peeling;
- the films include two polyethylene sheets, one of which is in ultra low density polyethylene.

Other features and advantages of the invention will become apparent during the description hereafter, with reference to the appended figures:

DESCRIPTION OF THE DRAWINGS

FIG. 3 is a view of the drape of FIG. 2 after applying an adhesive;

FIG. 4 is a view of the top face of the drape after placement of absorbent strips;

DESCRIPTION OF THE PREFERRED EMBODIMENT

Figure 1:
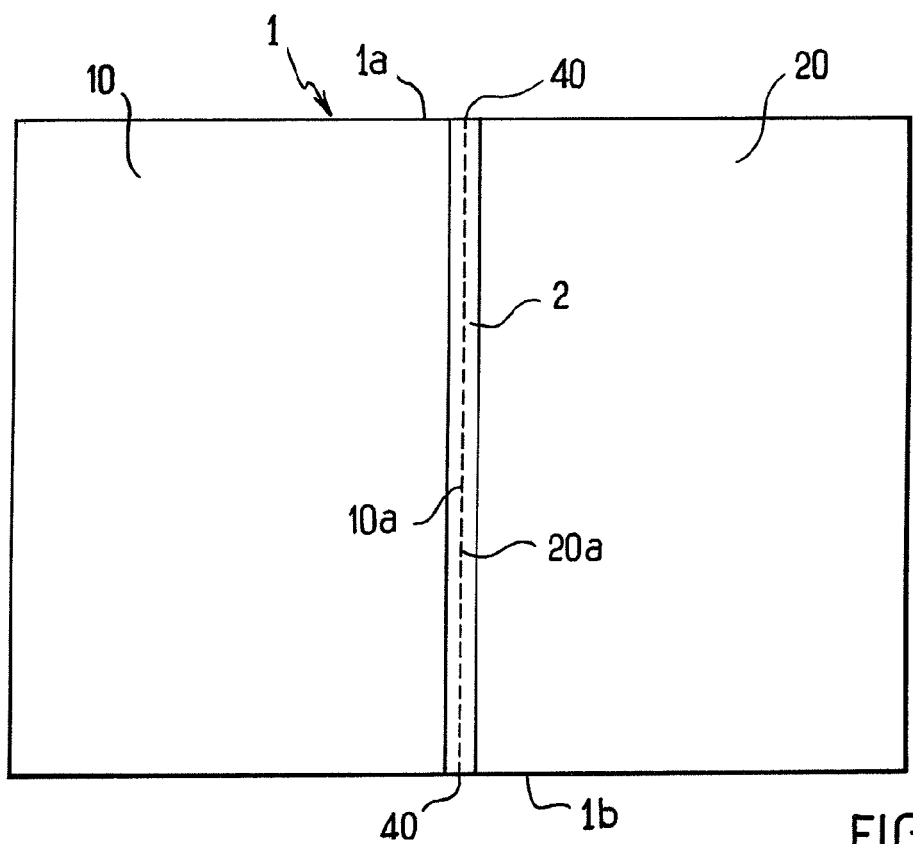
FIG. 1 is a view of the underside of an embodiment of a drape according to the invention, i.e. the face which will be in contact with the skin of a patient before the window is made.
Figure 2:
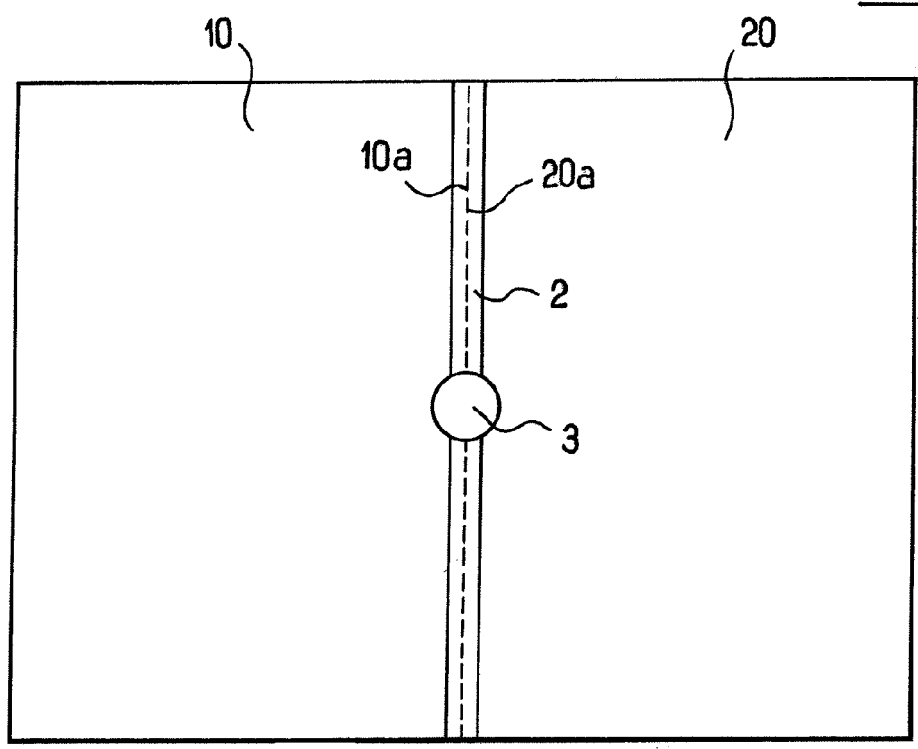
FIG. 2 is a view of the drape of FIG. 1 after having made a window.

With reference to FIGS. 1-3, we shall now describe a first embodiment of a drape (1) according to the invention. The drape (1) comprises two rectangular impermeable peelable films (10, 20), for example of about 100 cm×70 cm, two edges (10a, 20a) of which are joined. Under these edges, the films are attached to an impermeable peelable strip (2), for example with a width of about 5-10 cm, by a heat weld allowing subsequent detachment of the films of the strip by peeling. By peelable film (strip) is meant a film (strip) formed with two superposed polyethylene sheets, one of which is in ultra low density polyethylene. The ultra low density polyethylene sheet is thin in thickness, while the other polyethylene sheet is thick. The heat weld is achieved while the ultra low density polyethylene sheet of the films is in contact with the polyethylene sheet of the strip or vice versa. Alternatively, the heat weld is achieved while the ultra low density polyethylene sheet of the films is in contact with the ultra low density polyethylene sheet of the strip. Heat welding consists in locally melting these ultra low density polyethylene sheets. Indeed, during heat welding, the ultra low density polyethylene sheet with thin thickness has a lower melting temperature than that of the thick polyethylene sheet which itself does not melt during this welding.

It should be noted that in this way, during heat welding, the ultra low density polyethylene sheets adhere together and during peeling, the mechanical tear resistance of both of these sheets is very small.

In the drape (1), a hole is made, forming a window (3) shared between both films, for example in two substantially equal portions. This window has all the intended shapes and dimensions, for example a circular shape (as illustrated in FIG. 2) or an oval shape. Adhesive (4) is applied around the hole on the underside of the drape and this adhesive, like the hole, is temporarily protected by a silicone paper (5) which will be removed for attaching the drape around the surgical site.

On the top side of the drape, as illustrated in FIG. 4, three U strips (6, 7) in an absorbent material, for example non-woven fabric, are adhesively attached around the hole (3). Both strips are placed in opposition so that their wings overlap on a cutting line (40) and are not attached to the location of the overlapping or to the drape, or together. For example, the U strips form an inner square with a side of about 40 cm and an outer square with a side of about 50-60 cm. Inside the square of about 40 cm, all the materials except the silicone paper, are preferably transparent.

Alternatively, the drape includes in a way known per se, several superposed windows, the size of which decreases from the initial window of the drape up to the topmost located window.

Figure 5:
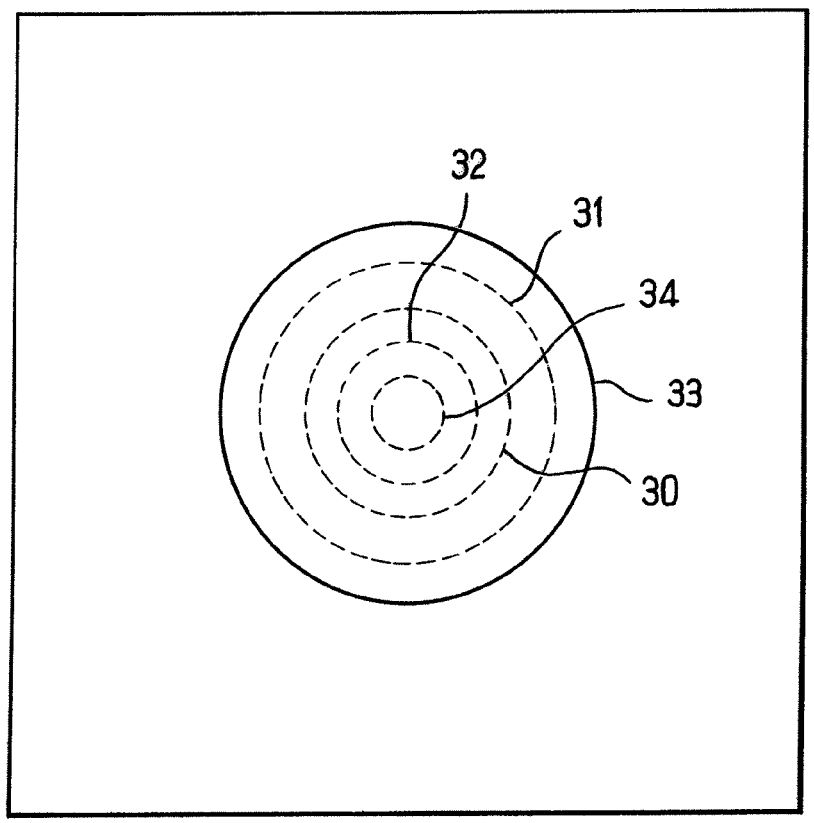
FIG. 5 is a schematic view of the drape of FIGS. 1-4 modified with several superposed windows.

FIG. 5 illustrates a drape which includes an initial window (30), for example with a diameter of about 15 cm, covered with a first peelable adhesive mask (31) itself including a window (32), for example with a diameter of about 10 cm, which is covered by a second peelable adhesive mask (33) provided with a window (34) with for example a diameter of about 5 cm. With the exception of the window shown in FIG. 5, the drape of FIG. 5 is as shown in FIGS. 1-4. The masks are slit in order to allow lateral peeling.

We shall now describe the use of such an operating drape. For laying the drape, the silicone paper is removed. The drape is then applied on the skin of the patient. For this, the transparent square provides visibility through the surgical site. The operation is then performed and permanent lines (perfusion, arterial pressure measurement and other measurements) are set into place. Next, one of the films is separated from the strip by peeling the film laterally up to the whole of the surgical site. Next, the drape is pulled laterally around the lines, the U strips also moving away without providing resistance around the installed lines. The drape is then detached from the skin of the patient before pulling it laterally.

It should be noted that the U strips are used for absorbing the liquids during the operation and the non-woven square may be oriented so as to avoid having in the low position of the drape, in terms of gravity, sides where the strips overlap.

Figure 6:
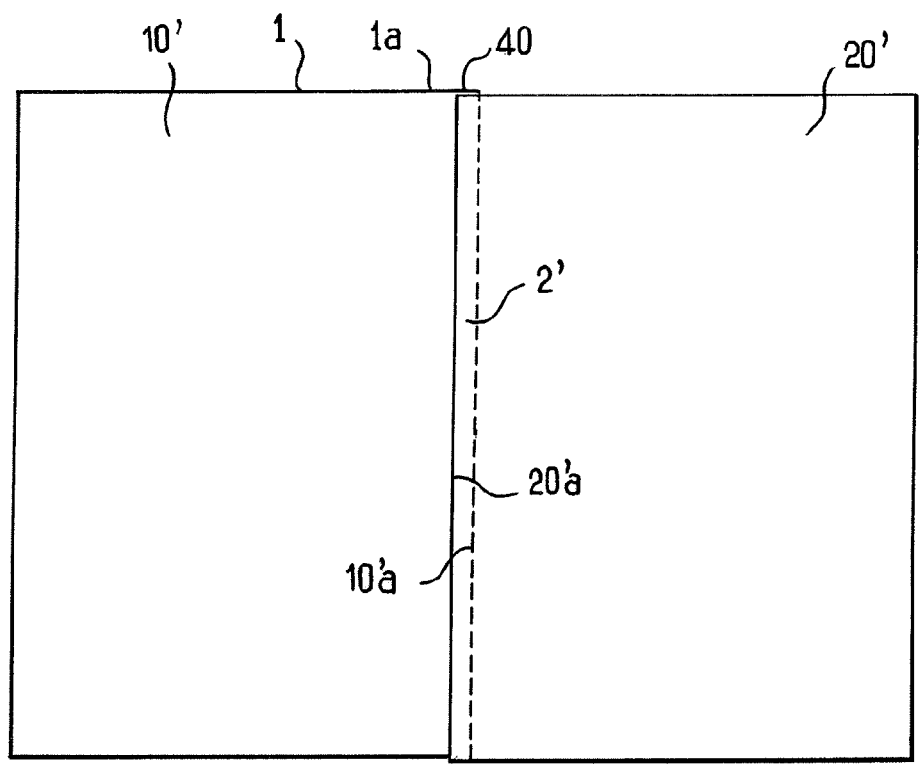
FIG. 6 is a view of the face of an alternative embodiment of a drape according to the invention, before the window is made.
Figure 7:
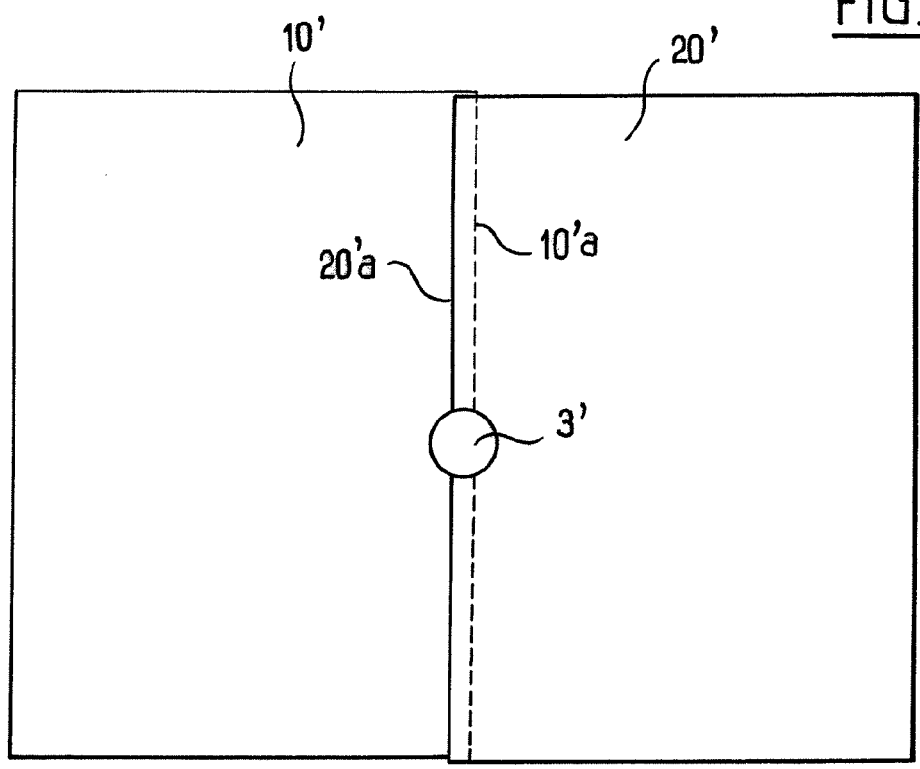
FIG. 7 is a view of the drape of FIG. 6 after having made the window.

With reference to FIGS. 6 and 7, we shall describe an alternative embodiment of a drape according to the invention. In this alternative embodiment, both films (10', 20') of the drape have two superposed edges (10'$a$, 20'$a$) and a heat weld (2') allowing for the peeling to be carried out between the thereby superposed edges. The overlap of both films is for example with a width of about 5 cm. During this overlapping, the ultra low density polyethylene sheet of one (20') of the films is in contact on this overlap with the polyethylene sheet of the other one (10') of the films. Alternatively, during this overlapping, the ultra low density polyethylene sheet of one (20') of the films is in contact on this overlap with the ultra low density polyethylene sheet of the other one (10') of the films. Heat welding consists in melting ultra low density polyethylene sheets at the overlap. A hole (3') is made in the same way as the hole (3) was made earlier.

The invention is not limited to the embodiments which have been described.

The invention claimed is:

1. An operating drape having a window through which a device can be extended to a surgical site, said operating drape comprising
    a first impermeable film,
    a second impermeable film,
    a bond comprising a heat weld between a margin of a surface of said first impermeable film and a margin of a surface of said second impermeable film, said bond being strong enough to maintain said first film and said second film in extension of one another, and having a tear resistance small enough to permit said first film and said second film to be peeled apart, the window being shared between the first film and the second film, a border of said window being opened when said first film and said second film are peeled apart thereby permitting removal of said drape without dislodgement of said device.

2. The operating drape according to claim 1, wherein said bond further comprises an impermeable strip heat welded to said margin of said first film and to said margin of said second film, thereby maintaining said margin of said first film and said margin of said second film in mutual parallel juxtaposition, said heat seal bond being releasable for permitting said impermeable strip and at least one of said first film and said second film to be peeled apart for separation of said first film from said second film.

3. The operating drape according to claim 1, wherein the first film and the second film have respective superposed edges, the heat weld being between said edges.

4. The operating drape according to claim 3, wherein the edges are rectilinear.

5. The operating drape according to claim 1 wherein the window is substantially half-shared between the first film and the second film.

6. The operating drape according to claim 1 wherein the first film and the second film are rectangular.

7. The operating drape according to claim 1 further comprising an absorbent material affixed to said first film and said second film around the window, there being a slit in said absorbent material for permitting lateral peeling of said first film away from said second film.

8. The operating drape according to claim 7, wherein the absorbent material comprises two mating absorbent strips for forming a frame around the window and overlapping, the strips being adhesively bonded to the drape except in locations where the strips overlap so that they remain free in these locations.

9. The operating drape according to claim 8, wherein the absorbent strips are U-shaped.

\* \* \* \* \*